(12) United States Patent
Yamashita et al.

(10) Patent No.: US 11,435,822 B2
(45) Date of Patent: Sep. 6, 2022

(54) ESTIMATION METHOD, ESTIMATION PROGRAM, AND ESTIMATION DEVICE

(71) Applicant: Nippon Telegraph and Telephone Corporation, Tokyo (JP)

(72) Inventors: Jumpei Yamashita, Tokyo (JP); Hidetaka Koya, Tokyo (JP); Hajime Nakajima, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 5 days.

(21) Appl. No.: 17/052,458

(22) PCT Filed: May 9, 2019

(86) PCT No.: PCT/JP2019/018623
§ 371 (c)(1),
(2) Date: Nov. 2, 2020

(87) PCT Pub. No.: WO2019/216387
PCT Pub. Date: Nov. 14, 2019

(65) Prior Publication Data
US 2021/0048882 A1   Feb. 18, 2021

(30) Foreign Application Priority Data
May 9, 2018  (JP) .............................. JP2018-090711

(51) Int. Cl.
*G06F 3/01* (2006.01)
*A61B 5/297* (2021.01)
(Continued)

(52) U.S. Cl.
CPC .............. *G06F 3/013* (2013.01); *A61B 5/163* (2017.08); *A61B 5/297* (2021.01); *G06F 3/012* (2013.01); *A61B 5/1114* (2013.01)

(58) Field of Classification Search
CPC ......... G06F 3/013; G06F 3/012; A61B 5/163; A61B 5/1114; A61B 5/297
See application file for complete search history.

(56) References Cited

U.S. PATENT DOCUMENTS 5,360,971 A * 11/1994 Kaufman ............... A61B 3/113
                                                    250/221
5,689,619 A * 11/1997 Smyth .................... B60K 35/00
                                                    706/45
(Continued)

FOREIGN PATENT DOCUMENTS

JP     2014-211794    11/2014
JP     2017-049775     3/2017

OTHER PUBLICATIONS

Ohtani et al., "Temporal Characteristics of the Eyeball Motions," Ergonomics, 1968, 4(1):29-36, Abstract.

*Primary Examiner* — Mihir K Rayan
(74) *Attorney, Agent, or Firm* — Fish & Richardson P.C.

(57) ABSTRACT

An estimation method includes first acquiring information of an eyeball motion of a user on the basis of a measurement value of an eye potential of the user, second acquiring positional information of an interaction target on a screen that corresponds to an interaction performed on a device through an operation of the user, third acquiring information regarding a relative motion of sight of the user on the basis at least of the information of the eyeball motion of the user, and estimating a sight position of the user on the screen on the basis of the information regarding the relative motion of the sight of the user and the positional information of the interaction target on the screen, by processing circuitry.

7 Claims, 13 Drawing Sheets

(51) Int. Cl.
*A61B 5/16* (2006.01)
*A61B 5/11* (2006.01)

(56) References Cited

U.S. PATENT DOCUMENTS

| | | | | |
|---|---|---|---|---|
| 6,323,884 | B1* | 11/2001 | Bird | G06F 3/04812 |
| | | | | 715/810 |
| 8,333,475 | B2* | 12/2012 | Sugio | A61B 5/398 |
| | | | | 351/205 |
| 8,793,620 | B2* | 7/2014 | Stafford | G06F 3/013 |
| | | | | 715/862 |
| 9,507,418 | B2* | 11/2016 | Yu | G06F 3/0482 |
| 10,871,874 | B2* | 12/2020 | Sullivan | G06F 3/0487 |
| 2009/0289895 | A1* | 11/2009 | Nakada | G06F 3/013 |
| | | | | 345/157 |
| 2014/0022157 | A1 | 1/2014 | Lee et al. | |
| 2017/0060252 | A1 | 3/2017 | Komaki et al. | |
| 2018/0088678 | A1 | 3/2018 | Komaki et al. | |
| 2018/0120934 | A1 | 5/2018 | Taguchi | |
| 2019/0073044 | A1 | 3/2019 | Komaki et al. | |

* cited by examiner

ESTIMATION METHOD, ESTIMATION PROGRAM, AND ESTIMATION DEVICE

CROSS-REFERENCE TO RELATED APPLICATIONS

This application is a National Stage application under 35 U.S.C. § 371 of International Application No. PCT/JP2019/018623, having an International Filing Date of May 9, 2019, which claims priority to Japanese Application Serial No. 2018-090711, filed on May 9, 2018. The disclosure of the prior application is considered part of the disclosure of this application, and is incorporated in its entirety into this application.

TECHNICAL FIELD

The present invention relates to an estimation method, an estimation program, and an estimation apparatus.

BACKGROUND ART

If it is possible to acquire which position on a screen the sight of a user who is performing operations mainly on the screen using a device is directed to, it is possible to use the information for analysis regarding an input interface and a user state. For such a purpose, an eye tracking system configured to acquire a user's sight position has been proposed.

Incidentally, many related art technologies use eye tracking systems configured to acquire absolute positions of sight by imaging the eyeballs of the users and the vicinity of their eyeballs from a side in front using incorporated cameras and processing the obtained image data using algorithms when sight positions are measured. However, the method has some problems.

First, many of the related art eye tracking systems are expensive, and it is difficult to introduce the systems to sites. Also, because the related art eye tracking systems peripherally acquire highly confidential information such as users' faces and living rooms in addition to the sight information, there may be cases in which the eye tracking systems cannot be used from the viewpoint of security. Further, the related art eye tracking systems estimate only users' sight positions in screens and cannot acquire states in which the users are looking at targets that are present away from the screen due to constraints that the image processing scheme has.

In addition, the related art eye tracking systems cannot perform calculation if specifications of the devices are insufficient in a case in which it is attempted to perform the calculation for estimating the sight positions on the devices (such as PCs, tablets, and smartphones) that the users are using for operations because large-volume video image data has to be processed.

Note that although there are also types adapted such that small-sized cameras for imaging the eyes are secured on the side of faces, and the method enables acquisition of sight positions regardless of whether inside or outside of the screen the sight positions are located, the method incurs yet higher costs than the related art stationary-type eye trackers in the related art and is not typically used.

As a method that can solve these problems, there is a method for estimating sight positions using an electrooculogram (EOG) method. The EOG method is a technique for measuring eyeball motions instead of sight positions. This is a technique for estimating directions and amount of eyeball motions from changes in potential by attaching electrodes to the vicinity of the eyeballs using the fact that the eyeballs have positive potentials on the front side and negative potentials on the back side (Non-Patent Literature 1).

According to the EOG method, eyeball motions are measured using only the potentials acquired by the several electrodes. Thus, expensive devices are not required, confidential peripheral information is not acquired, and the amount of calculation necessary for estimation is smaller than that necessary for image processing.

CITATION LIST

Non-Patent Literature

Non-Patent Document 1: Akira Otani, "Temporal Characteristics of the Eyeball Motions", Ergonomics, vol. 4, No. 1, pp. 29-36

SUMMARY OF THE INVENTION

Technical Problem

The EOG method can be categorized into two methods, namely an AC EOG method and a DC EOG method on the basis of potential processing methods.

Among these, the DC EOG method is adapted such that a potential state in the vicinity of the eyeballs is directly acquired, and it is thus possible to acquire the potential including information regarding absolute positions of the eyeballs. However, large drifts occur in the DC EOG method. The drifts are phenomena in which baselines of measured potentials change with elapse of time. Although a method for correcting the drifts has already been proposed, the method is not perfect, and it is difficult to actually measure the sight positions.

Meanwhile, according to the AC EOG method, it is possible to acquire potentials including information regarding relative motions of eyeballs while avoiding influences of drifts, which will be described later, to some extent by acquiring amount of change in potential state in the vicinity of eyeballs. However, because the AC EOG method is designed only for measuring eyeball motions, the acquired data includes information regarding relative motions of sight but does not include information regarding absolute positions of sight.

Thus, several methods for estimating sight positions using eyeball motions acquired by the AC EOG method have been proposed in the related art. FIGS. 13(a) and 13(b) are diagrams for explaining a sight position estimation method in the related art. The method in the related basically includes associating how much sight moves on a screen when a certain eyeball motion is performed (the movement amount is associated) and acquiring an absolute position at a certain timing (for example, the position of the click C1 in FIG. 13(a)) by a method other than EOG (identification of the absolute position). In addition, the method further includes continuously adding sight movement amounts from the timing to estimate a sight position P2' in the method (see FIG. 13(b)).

However, the method in the related art is not practical because estimation accuracy is degraded with the elapse of time. In other words, errors become cumulative with the elapse of time, and the distance between an actual sight position P2 (see FIG. 13(b)) and the estimated sight position P2' deviates in the method in the related art. The reasons for this are as follows.

First, an error occurs when a relative movement amount is estimated in the method in the related art. As one of the causes of the error, noise mixed into a change in potential is conceivable. According to the method in the related art, it is not possible to completely eliminate drifts by an AC amplifier with a potential of an apparatus to which the AC EOG method is applied even if the drifts are eliminated to some extent. Also, a considerable error occurs in the estimation of the movement amount because noise caused for other various reasons cannot be completely removed in the method in the related art.

Additionally, if a time elapses after the movement amount is associated, an error due to a change in relationship between the eyeball motion amount and the amount of sight movement further occurs. This is mainly because the posture changes with elapse of a long period of time. For example, even if the eyeball motion amount is the same, the amount of sight movement is large in a case in which the screen is seen from a far location while the amount of sight movement is small in a case in which the screen is seen from a close location. Although it is possible to address this problem by a method of acquiring information regarding the posture of the user from another sensor in addition to the eyeball motion, this measure is also considered not to be perfect.

In addition, the information regarding the absolute position of sight is not acquired at all in the AC EOG method. Thus, errors with respect to the estimated values of movement amounts are continuously accumulated with elapse of time in the method in the related art. It is difficult to perform estimation by the method in the related art when a time during which absolute position identification is not performed continues for a long time even if the errors are reduced using various methods.

It is thus possible to recognize that repeating two types of correction for association of the movement amount and identification of the absolute position every time an event such as elapse of a specific time or more or a motion of a head of a user occurs is appropriate to precisely estimate the sight position using the AC EOG method in the method in the related art.

However, the user is required to gaze at a certain point, move the sight by a specific amount, or the like in order to perform the correction in the method in the related art. Frequently performing correction and asking for the operation of gazing at a point, moving the sight, and the like every time the correction is performed as in the method in the related art are troublesome to the user and are not practical.

For the reason that accuracy is degraded if no correction is performed while practical usability is degraded if the correction is performed as described above, it is difficult to practically use the sight position estimation based on the AC EOG method.

The present invention was made in view of the aforementioned circumstances, and an object of the present invention is to provide an estimation method, an estimation program, and an estimation apparatus that enable sight position measurement with high accuracy by applying the AC EOG method without degrading practical usability.

Means for Solving the Problem

In order to solve the aforementioned problem and to achieve the object, an estimation method according to the present invention is an estimation method including: first acquiring information of an eyeball motion of a user on the basis of a measurement value of an eye potential of the user; second acquiring positional information of an interaction target on a screen that corresponds to an interaction performed on a device through an operation of the user; third acquiring information regarding a relative motion of sight of the user on the basis at least of the information of the eyeball motion of the user; and estimating a sight position of the user on the screen on the basis of the information regarding the relative motion of the sight of the user and the positional information of the interaction target on the screen, by processing circuitry.

Effects of the Invention

According to the present invention, it is possible to perform sight position measurement with high accuracy by applying the AC EOG method without degrading practical usability.

DESCRIPTION OF EMBODIMENTS

Hereinafter, an embodiment of the present invention will be described in detail with reference to drawings. Note that the present disclosure is not limited by the embodiment. Also, the same components in description of the drawings will be represented with the same reference signs.

First Embodiment

Figure 1:
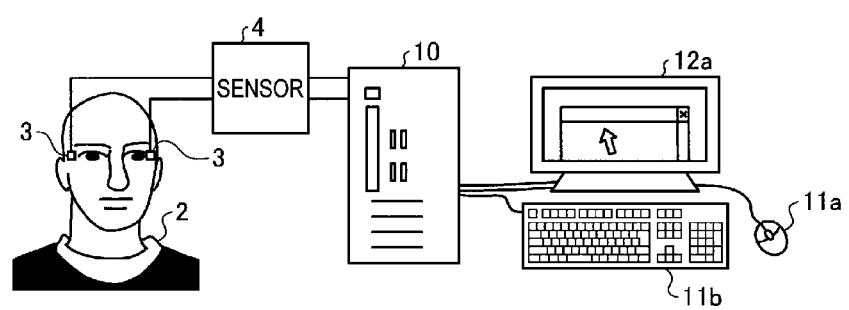
FIG. 1 is a diagram illustrating an example of a configuration of an estimation system according to a first embodiment.

First, a first embodiment of the present invention will be described. FIG. 1 is a diagram illustrating an example of a configuration of an estimation system according to the first embodiment.

As illustrated in FIG. 1, the estimation system according to the embodiment has a sensor 4 connected to a plurality of electrodes 3 that are attached to the vicinity of eyeballs (temples, for example) of a user 2 and an estimation apparatus 10 configured to receive an input of a measurement value of an eye potential from the electrodes 3 and estimate a sight position of the user on a screen. The estimation apparatus 10 is connected to a mouse 11a and a keyboard 11b, which are user interfaces, and a display 12a configured to display a screen image in accordance with an operation performed by the user on the user interfaces.

The sensor 4 measures a temporal change in eye potential through the electrodes 3 that are in contact with the vicinity of the eyeballs of the user 2. The measurement result is input to the estimation apparatus 10. Note that the number of the electrodes 3 may be two or more.

The estimation apparatus 10 acquires information of an eyeball motion of the user (the amount of change in eye potential) on the basis of the amount of temporal change in eye potential of the user. Further, the estimation apparatus 10 acquires positional information of an interaction target on a screen that corresponds to an interaction performed on a device (the mouse 11a or the keyboard 11b) through an operation of the user. The interaction is an action of pressing a button or the like on the screen. When the user performs an interaction, the user has to gaze at a target of the action (a mouse cursor, a button on which a finger of the user himself/herself is placed for tapping it, a cursor when a text is input, or the like). In the estimation apparatus 10, the timing is captured, and the position of the interaction target on the screen is used as a provisional absolute position of sight.

In addition, the estimation apparatus 10 acquires information regarding a relative motion of sight of the user on the basis of the information of the eyeball motion of the user. In other words, the estimation apparatus 10 converts the amount of change in eye potential and acquires the amount of sight movement (relative value) that corresponds to the amount of change in eye potential. Next, the estimation apparatus 10 estimates the sight position of the user on the screen by adding the amount of sight movement (relative value) converted from the amount of change in potential to the positional information (absolute value) of the interaction target on the screen.

In this manner, the estimation apparatus 10 practically realizes eye tracking by adding the amount of sight movement obtained from the eyeball motion obtained by the AC EOG method on the basis of the absolute position of the sight obtained on the basis of the interaction information.

Configuration of Estimation Apparatus

Figure 2:
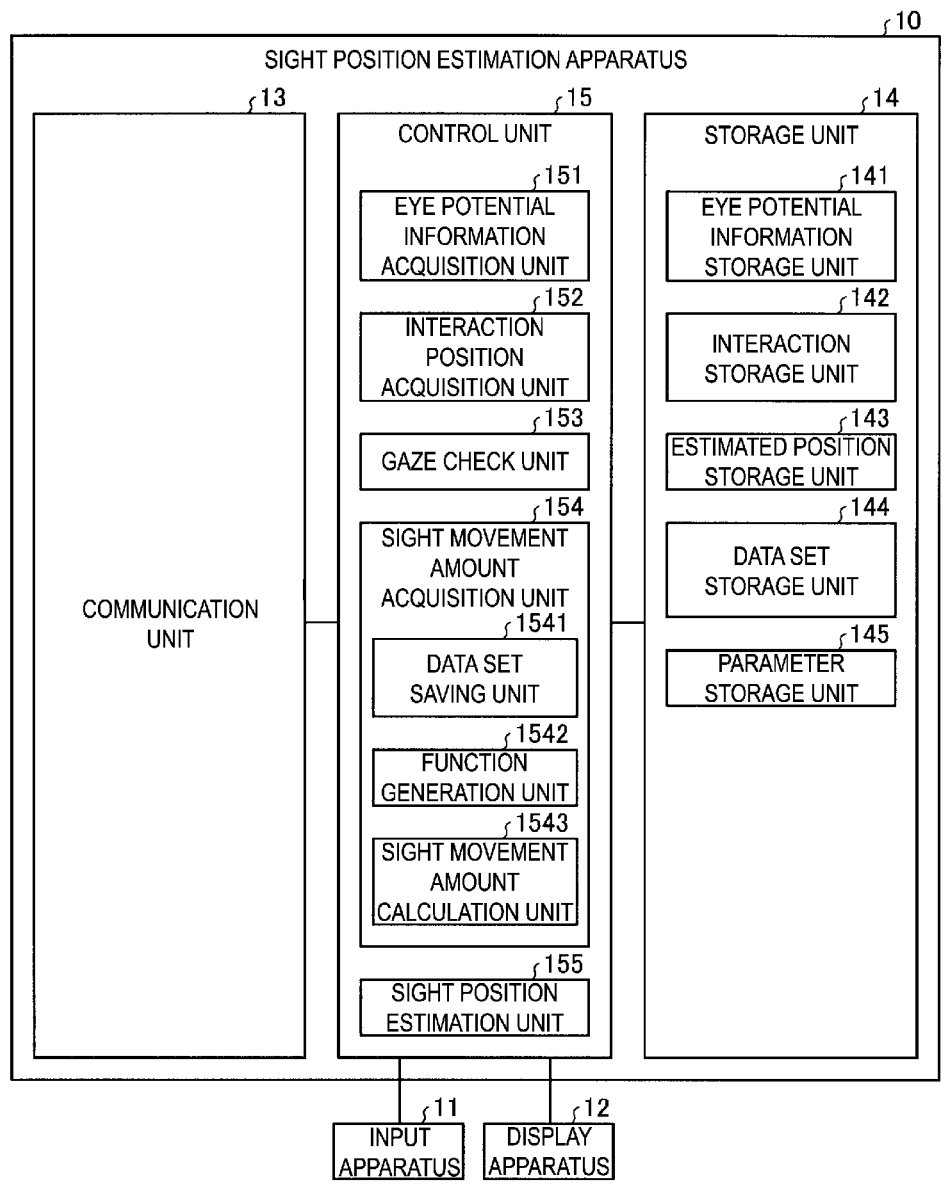
FIG. 2 is a block diagram illustrating an example of a configuration of an estimation apparatus illustrated in FIG. 1.

Next, a configuration of the estimation apparatus 10 will be described. FIG. 2 is a block diagram illustrating an example of a configuration of the estimation apparatus 10 illustrated in FIG. 1. As illustrated in FIG. 1, the estimation apparatus 10 is connected to an input apparatus 11 and a display apparatus 12. Also, the estimation apparatus 10 has a communication unit 13, a storage unit 14, and a control unit 15.

The input apparatus 11 is a device apparatus configured to receive inputs of various pieces of instruction information for the control unit 15 in response to input operations performed by the user. For example, the input apparatus 11 is realized using input devices such as the mouse 11a and the keyboard 11b.

A cursor or a slider on a screen of the display apparatus 12 moves in response to an interaction performed by the user through an operation of moving the mouse 11a. The position of the cursor or the slider on the screen is acquired by an interaction position acquisition unit 152 (which will be described later) as positional information of the interaction target on the screen. Also, a button on the screen is selected in accordance with an interaction performed by the user through an operation of clicking the mouse 11a. The position of the button on the screen is acquired by the interaction position acquisition unit 152 (which will be described later) as positional information of the interaction target on the screen.

Then, letters and the like are described in a file on the screen in accordance with the interaction performed by the user through an operation of the keyboard 11b. The position of the described letters and the like is acquired by the interaction position acquisition unit 152 (which will be described later) as positional information of the interaction target on the screen.

The display apparatus 12 is realized by a display 12a such as a liquid crystal display. Specifically, the display apparatus 12 displays an application screen and the like.

The communication unit 13 is a communication interface configured to transmit and receive various pieces of information to and from other apparatuses connected via a network or the like. The communication unit 13 is realized by a network interface card (NIC) or the like and performs communication between other apparatuses and the control unit 15 (which will be described later) via an electrical communication line such as a local area network (LAN) or the Internet.

The storage unit 14 is realized by a semiconductor memory element such as a random access memory (RAM) or a flash memory or a storage apparatus such as a hard disk or an optical disc, and a processing program for causing the estimation apparatus 10 to operate, data used during execution of the processing program, and the like are stored in the storage apparatus. The storage unit 14 has an eye potential information storage unit 141, an interaction storage unit 142, an estimated position storage unit 143, a data set storage unit 144, and a parameter storage unit 145.

The eye potential information storage unit 141 associates and stores the amount of change in eye potential based on the measurement value of the eye potential obtained by the sensor 4, the input of which has been received, with temporal information.

The interaction storage unit 142 associates and stores the positional information of the interaction target on the screen that corresponds to the interaction performed on the device through the operation of the user with temporal information. For example, the interaction storage unit 142 associates and stores the position of the cursor or the slider on the screen of the display apparatus 12 that has moved in response to the interaction performed by the user through the operation of moving the mouse 11a with temporal information. Also, the interaction storage unit 142 stores, as temporal information, the positional information of the button on the screen selected in response to an interaction performed by the user through an operation of clicking the mouse 11a. In addition, the interaction storage unit 142 associates and stores the position of the letters described in the file on the screen in response to the interaction performed by the user through the operation of the keyboard 11b with temporal information.

The estimated position storage unit 143 associates and stores the sight positional information of the user on the screen, which has been estimated by the sight position estimation unit 157, with temporal information.

The data set storage unit 144 associates and stores the information of the eyeball motion of the user with the positional information of the interaction target on the screen. The data set storage unit 144 stores a plurality of data sets by regarding the amount of change in eye potential of the user and the positional information of the interaction target on the screen that corresponds to the amount of change as one data set.

The parameter storage unit 145 stores arithmetic expressions used to calculate the amount of sight movement and various parameters applied to the arithmetic expressions. The parameters stored in the parameter storage unit 145 are updated by a function generation unit 1542 (which will be described later).

The control unit 15 controls the entire estimation apparatus 10. The control unit 15 has an internal memory for storing a program and required data that define various processing procedures and the like and execute various types of processing using the programs and the data. For example, the control unit 15 is an electronic circuit such as a central processing unit (CPU) or a micro processing unit (MPU). In addition, the control unit 15 functions as various processing units by the various programs operating. The control unit 15 has an eye potential information acquisition unit 151 (first acquisition unit), an interaction position acquisition unit 152 (second acquisition unit), a gaze check unit 153 (determination unit), a sight movement amount acquisition unit 154 (third acquisition unit), and a sight position estimation unit 155.

The eye potential information acquisition unit 151 acquires information of the eyeball motion of the user (the amount of change in eye potential) on the basis of the measurement value of the eye potential of the user, which has been input by the sensor 4. The eye potential information acquisition unit 151 associates the acquired amount of change in eye potential with time information, outputs the amount of change in eye potential with the time information to the gaze check unit 153, and also stores the amount of change in eye potential with the temporal information in the eye potential information storage unit 141.

The interaction position acquisition unit 152 acquires the positional information of the interaction target on the screen that corresponds to the interaction performed on the device (the mouse 11a and the keyboard 11b) through an operation of the user. The interaction position acquisition unit 152 associates the acquired positional information of the interaction target with temporal information, outputs the positional information of the interaction target with the temporal information to the gaze check unit 153, and also stores the positional information of the interaction target with the temporal information in the interaction storage unit 142.

The gaze check unit 153 determines whether or not a first distance that is a distance between a previously estimated sight position of the user on the screen and an actual position of the interaction target on the screen that corresponds to a new interaction is equal to or less than a predetermined threshold value L.

Only in accordance with a determination that the first distance is equal to or less than the predetermined threshold value, the gaze check unit 153 outputs the positional information of the interaction target on the screen in the new interaction and the corresponding amount of change in eye potential to the sight movement amount acquisition unit 154 and the sight position estimation unit 155. Also, the gaze check unit 153 holds the positional information of the interaction target on the screen in the new interaction and the corresponding amount of change in eye potential without outputting them to the sight movement amount acquisition unit 154 and the sight position estimation unit 155 in accordance with a determination that the first distance is larger than the predetermined threshold value. In this case, the held information may be used by the sight movement amount acquisition unit 154 along with data that passes the next gaze check. The gaze check unit 153 performs the determination every time an interaction occurs.

The sight movement amount acquisition unit 154 acquires information regarding a relative motion of sight of the user on the basis at least of information of an eyeball motion of the user. The sight movement amount acquisition unit 154 calculates the amount of relative movement of sight of the user on the screen. The sight movement amount acquisition unit 154 has a data set saving unit 1541, a function generation unit 1542, and a sight movement amount calculation unit 1543.

The data set saving unit 1541 saves, in the data set storage unit 144, the information of the eyeball motion of the user acquired by the eye potential information acquisition unit 151 and the positional information of the interaction target on the screen acquired by the interaction position acquisition unit 152 as one data set. Specifically, the data set saving unit 1541 saves the amount of change in eye potential and the position of the interaction target on the screen that corresponds to the amount of change in eye potential.

Also, the data set saving unit 1541 saves the positional information of the interaction target on the screen in the new interaction, the first distance of which has been determined to be equal to or less than the predetermined threshold value by the gaze check unit 153, and the information of the eyeball motion that corresponds to the new interaction (the amount of change in eye potential) in the data set storage unit 144 at this timing. Note that an upper limit is set for the number of data sets in the data set storage unit 144, and in a case in which the number of data sets exceeds the upper limit, the data set saving unit 1541 discards the one oldest data set among the data sets in the data set storage unit 144.

The function generation unit 1542 generates a function F when the number of data sets saved in the data set storage unit 144 exceeds a predetermined number (several tens to several hundreds). The function F is a function that outputs, as the amount of sight movement, the amount of movement (including the distance and the direction) (relative value) from the position of the interaction target in the previous interaction to the position of sight at a current clock time if the amount of change in eye potential from the clock time at which the previous interaction occurred to the current clock time is input.

The function generation unit 1542 generates the function F by causing an arbitrary algorithm to learn a plurality of data sets saved in the data set storage unit 144. In other words, the function generation unit 1542 sets a value of each parameter applied to the function F. The function generation unit 1542 stores generated parameters in the parameter storage unit 145. Also, the function generation unit 1542 updates the parameters of the function F every time the data sets are updated with a new data set after the generation of the function F. The function generation unit 1542 updates the parameters stored in the parameter storage unit 145 to the updated parameters.

The sight movement amount calculation unit 1543 calculates the amount of sight movement on the screen that corresponds to the eyeball motion amount of the user on the basis of the information of the eyeball motion of the user and the positional information of the interaction target on the screen. Specifically, the sight movement amount calculation unit 1543 calculates the amount of movement from the position of the interaction target in the previous interaction to the estimated position of the sight at the current clock time by inputting the amount of change in eye potential from the clock time at which the previous interaction occurred to the current clock time to the function F.

The sight position estimation unit 155 estimates the sight position of the user on the screen on the basis of the information regarding the relative motion of the sight of the user and the positional information of the interaction target on the screen. Specifically, the sight position estimation unit 155 obtains the estimated position of the sight position at the current clock time by adding the amount of sight movement on the screen that corresponds to the amount of change in eye potential of the user acquired by the sight movement amount calculation unit 1543 to the target position of the previous interaction on the screen. Note that the sight position estimation unit 155 estimates the sight position of the user on the screen in a case in which the gaze check unit 153 has determined that the first distance is equal to or less than the predetermined threshold value.

Information Acquisition Processing

Processing performed by the estimation apparatus 10 will be described. First, the user performs an operation while viewing the screen of the display apparatus 12. The sensor 4 measures a temporal change in eye potential through the electrodes 3 that are in contact with the vicinity of the eyeballs of the user. The measurement result obtained by the sensor 4 is acquired by the eye potential information acquisition unit 151. Here, description will be given on the assumption that the total amount of change in eye potential from a clock time at which a certain interaction X occurs to a clock time at which a next interaction X+1 occurs is $\Delta_{(X\ to\ X+1)}$.

The estimation apparatus 10 performs processing related to operations (web browsing, document creation using office software, data input operations on a working system, and the like) that the user performs on the screen. In parallel with these processes, the interaction position acquisition unit 152 acquires and stores the target position of the interaction, which the user has performed on a computer, on the screen (coordinates at which the mouse has been clicked, coordinates at which tapping has been performed on the touch panel, coordinates of a text cursor when input has been performed using a physical keyboard, or the like). Here, a target position of a certain interaction X on the screen is assumed to be P(X).

In addition, the data set saving unit 1541 in the sight movement amount acquisition unit 154 associates the amount of change in potential (eyeball motion amount) with the amount (distance) of movement between the interactions. Here, $\Delta_{(I\ to\ I+1)}$ is assumed to be a total amount of change in eye potential from an interaction target I to an interaction target I+1. This $\Delta_{(I\ to\ I+1)}$ corresponds to the total amount of eyeball motion occurring from the interaction target I to the interaction target I+1.

The data set saving unit 1541 associates the value of the total amount of change in eye potential $\Delta_{(I\ to\ I+1)}$ with the position P(I) of the interaction target I on the screen as one data set. The sight movement amount acquisition unit 154 enables calculation of the amount of sight movement on the screen from the amount of the eyeball motion on the basis of the correspondence relationship.

Specifically, the data set saving unit 1541 collects $\Delta$ and P for about several tens to several hundreds of interaction intervals. Then, the function generation unit 1542 generates the function F by learning the plurality of data sets stored in the data set storage unit 144 using an arbitrary algorithm. The function F is a function for converting the total amount of change in eye potential $\Delta_{(I\ to\ I+1)}$. into the amount of sight movement (P(I+1)−P(I)) on the screen that corresponds to the total amount of change in eye potential $\Delta_{(I\ to\ I+1)}$.

Figure 3:
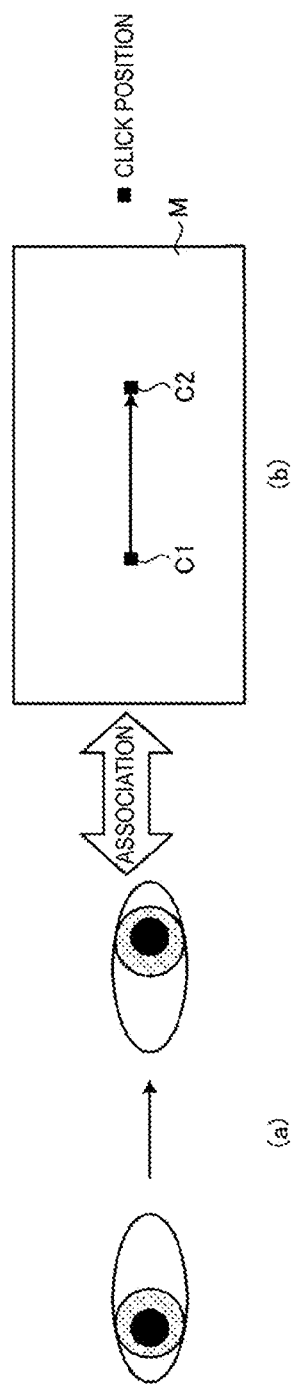
FIGS. 3(a) and 3(b) are diagrams for explaining association between an eyeball motion amount in the estimation apparatus illustrated in FIG. 2 and a position on a screen between two clicks.

FIGS. 3(*a*) and 3(*b*) are diagrams for explaining association between the eyeball motion amount in the estimation apparatus 10 illustrated in FIG. 2 and the position on a screen M between a click C1 and a click C2. As illustrated in FIGS. 3(*a*) and 3(*b*), the sight movement amount acquisition unit 154 associates the amount of eyeball motion performed between two clicks with the distance on the screen between the two clicks. Then, the sight movement amount acquisition unit 154 enables association of the total amount of change in eye potential with the amount of sight movement on the screen without any explicit operation of the user by enabling acquisition of the distance on the screen between the two clicks when the amount of eyeball motion performed between the two clicks is input using the function F.

Processing of Sight Position Estimation Unit

Next, processing of the sight position estimation unit 155 will be described. The sight position estimation unit 155 starts to estimate the position of sight in a stage in which the function F is completed. In the first embodiment, the sight position is regarded as being present at a target position P(m) of an interaction m on the screen when the interaction m in the past that is the closest to the clock time at which the sight position estimation is performed occurs.

The sight position estimation unit 155 adds an output $F(\Delta_{(m\ to\ now)})$ obtained by the sight movement amount calculation unit 1543 inputting the total amount of change in eye potential $\Delta_{(m\ to\ now)}$ from the clock time at which the interaction m occurs to the current clock time now to the function F, thereby obtaining the estimated position of the sight. The output $F(\Delta_{(m\ to\ now)})$ is the amount of movement (distance) from the position of the interaction target m to the position of the sight at the current clock time now that corresponds to $(\Delta_{(m\ to\ now)})$.

In other words, the sight position estimation unit 155 acquires the estimated position P(now) of the sight at the current clock time now using Equation (1) below.

[Math. 1]

$$P(\text{now})=P(m)+F(\Delta_{(m-now)}) \tag{1}$$

Figure 4:
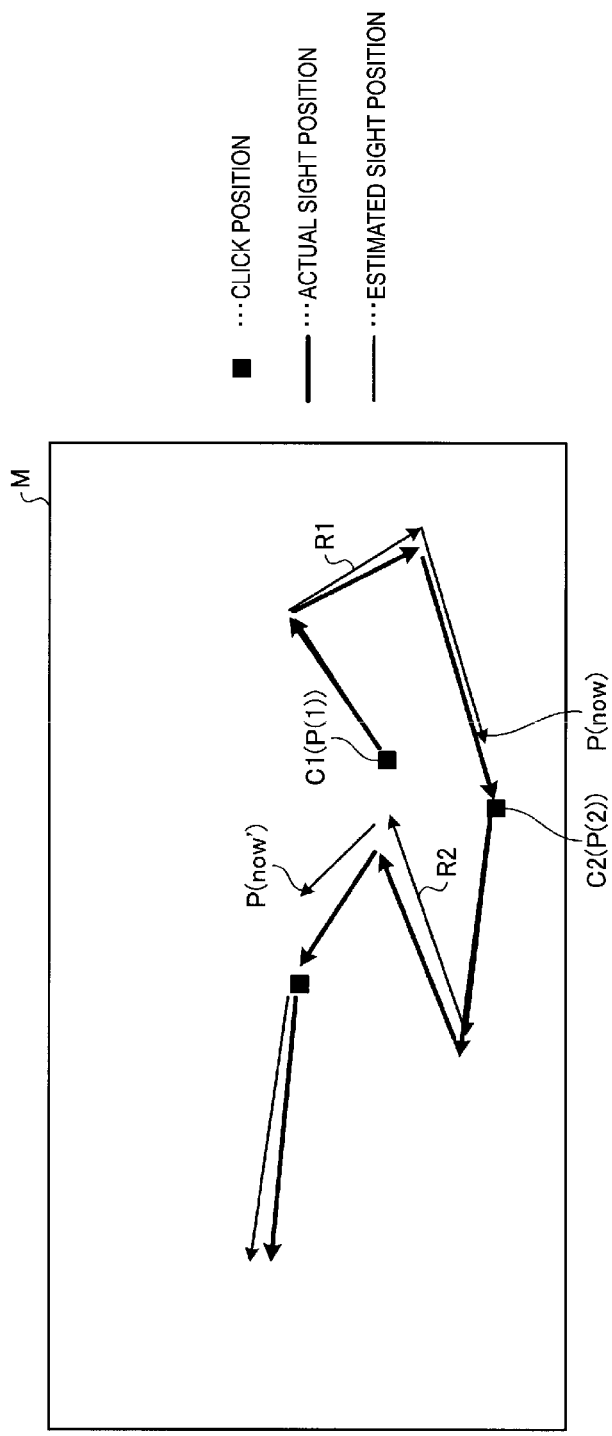
FIG. 4 is a diagram for explaining processing performed by a sight position estimation unit illustrated in FIG. 1.

FIG. 4 is a diagram for explaining processing of the sight position estimation unit 155 illustrated in FIG. 1. As illustrated in FIG. 4, the sight position estimation unit 155 estimates the sight position by adding sight movement amounts on the screen M converted from amount of change in eye potential at the position of the interaction (example: click) target on the screen M.

Specifically, if the position P(1) of the click C1 is input as the position of the interaction target, then the sight position estimation unit 155 acquires the sight position P(now) at the current clock time by sequentially adding each amount of sight movement on the screen M calculated on the basis of the amount of change in eye potential in each period to the position P(1) (see the arrow R1). If a position P(2) of the click C2 is newly input as a position of the interaction target, then the sight position estimation unit 155 calibrates the click position to the position P(2). Then, the sight position estimation unit 155 acquires the sight position P(now') on the screen M at the current clock time by sequentially adding each amount of sight movement calculated on the basis of the amount of change in eye potential in each period to the position (P(2)) (see the arrow R2).

Processing of Gaze Check Unit

Next, processing of the gaze check unit 153 will be described. Incidentally, the user does not necessarily perform the interaction while gazing at the interaction target on the screen. For example, the user may place a mouse cursor on a button first and then click the button while viewing another location. Nevertheless, an incorrect sight position is estimated if sight position estimation processing is performed in regard to all interactions.

Figure 5:
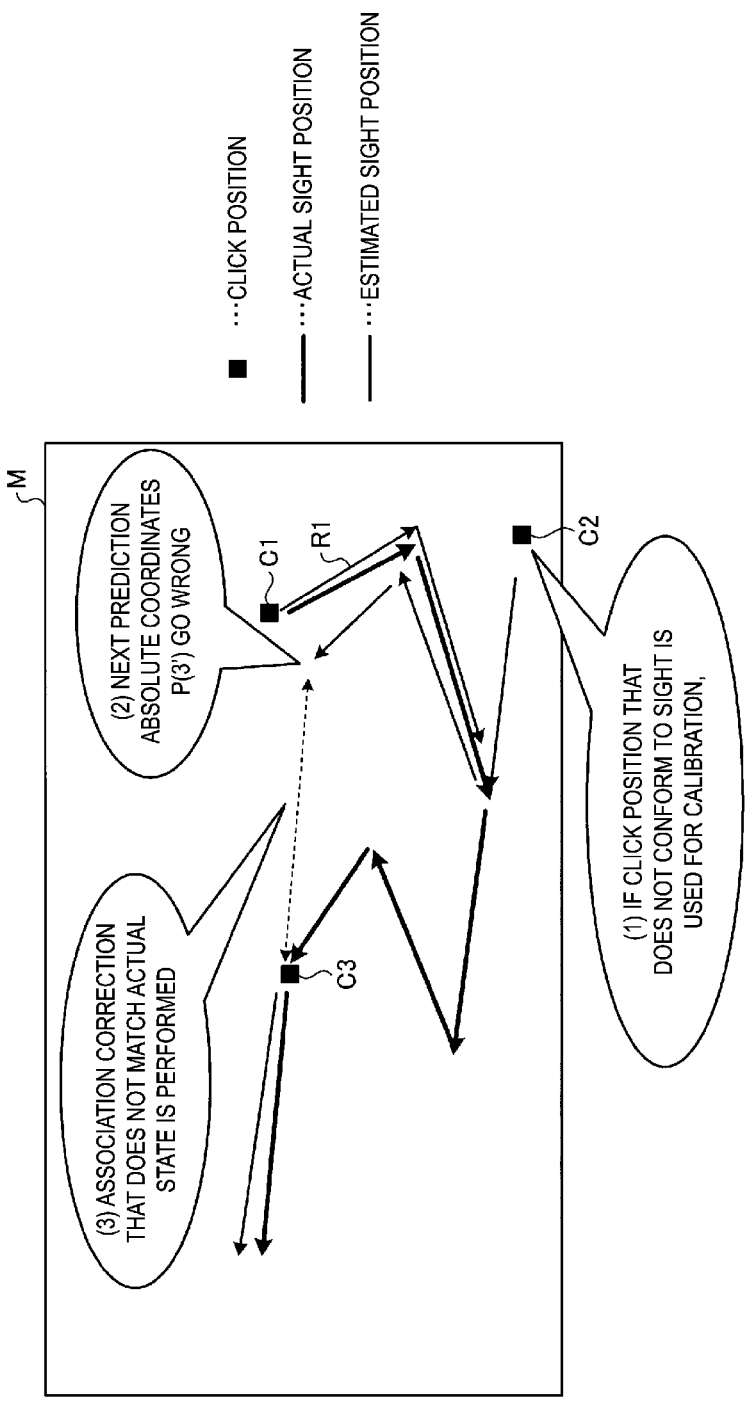
FIG. 5 is a diagram for explaining a deviation between an actual sight position and an estimated sight position.

FIG. 5 is a diagram for explaining a deviation between an actual sight position and an estimated sight position. If the click position C2 that does not conform to the sight is used for calibration as illustrated in the example of the screen M in FIG. 5 (see (1) of FIG. 5), absolute coordinates of a position P(3') predicted as the next sight position go wrong (see (2) of FIG. 5). Then, if the prediction result is used, association correction that does not match the actual state is performed (see (3) of FIG. 5).

Figure 6:
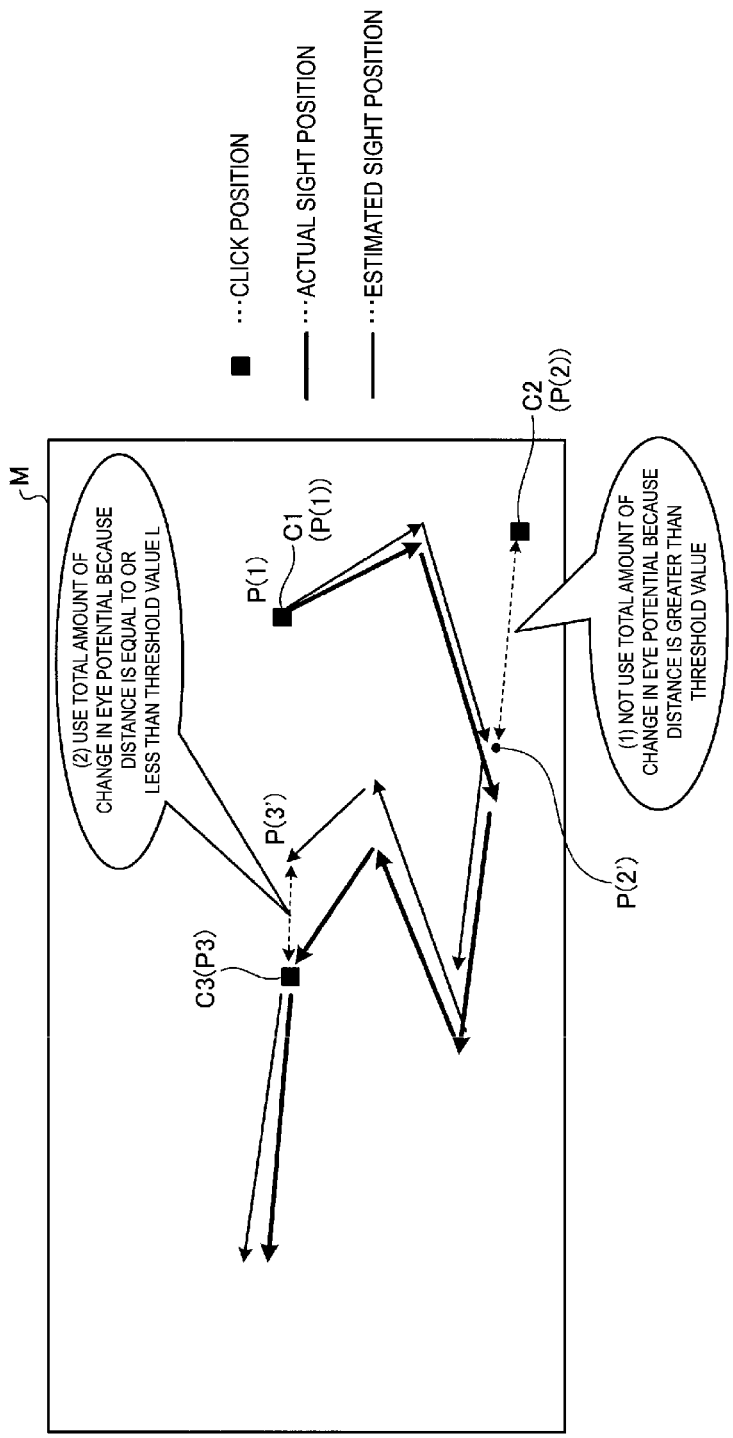
FIG. 6 is a diagram for explaining processing performed by a gaze check unit illustrated in FIG. 1.

Thus, the gaze check unit 153 performs gaze check every time an interaction occurs after a specific number of data sets are collected and the function F based on the data sets is generated. FIG. 6 is a diagram for explaining processing of the gaze check unit 153 illustrated in FIG. 1.

The gaze check unit 153 first sets a threshold value L. Next, the gaze check unit 153 obtains a distance (first distance) between a sight position $(P(n-1)+F\Delta_{(n-1\ to\ n)})$ estimated by adding the amount of sight movement until a clock time at which the current interaction n occurs in a case in which the interaction n−1 immediately before the current interaction n is regarded as a start point and the position P(n) of the current interaction n on the screen M. Then, the gaze check unit 153 determines whether or not the obtained first distance is smaller than the threshold value L.

For example, the gaze check unit 153 obtains the distance between a sight position $P(2')=((P(1)+F(\Delta_{(1\ to\ 2)})$ estimated by adding the amount of sight movement until a clock time at which the next click C2 occurs from the position P(1) to the position P(1) of the click C1 and a position P(2) of the next click C2 on the screen M. In this case, the first distance is greater than the threshold value L (see (1) of FIG. 6). In this case, because it is possible to determine that the actual sight position is deviated from the estimated sight position, the gaze check unit 153 does not use the total amount of change in eye potential $\Delta_{(1\ to\ 2)}$.

In a case in which the distance has not passed the check performed by the gaze check unit 153 in this manner, the update of the data set and the update of the parameters of the function F using the total amount of change in eye potential $\Delta_{(1\ to\ 2)}$ are not executed. Thus, the sight position estimation unit 155 uses the function F based on interaction information until the previous interactions to estimate the sight position of the user. In other words, the estimated sight position is $P(n-1)+F_{old}(\Delta_{(n-1\ to\ now)})$.

Next, the gaze check unit 153 obtains the distance between the estimated sight position $P(3')=((P(2)+F(\Delta_{(2\ to\ 3)}))$ and the position P(3) of the next click C3 on the screen. In this case, the obtained distance is equal to or less than the threshold value L (see (2) of FIG. 6). In this case, the gaze check unit 153 uses, as a data set, the total amount of change in eye potential $\Delta_{(2\ to\ 3)}$ and the position P(2) of the click C3 on the screen M.

Therefore, in a case in which the distance has passed the gaze check performed by the gaze check unit 153, the data set saving unit 1541 newly stores the total amount of change in eye potential $\Delta_{(n-1\ to\ n)}$ and the position P(2) in the data set storage unit 144. The upper limit is set for the number of data sets in the data set storage unit 144, and the data set saving unit 1541 discards a data set of the one oldest total amount of change in eye potential $\Delta(\ )$ among the data sets in the data set storage unit 144 in a case in which the number of data sets exceeds the upper limit. Note that the estimation apparatus 10 may accumulate data without deleting the old data set in the data set storage unit 144, select only the recent interaction among the accumulated data sets, and update the function F in order to select an optimal data set.

Update of Parameters of Function

Next, the function generation unit 1542 updates the parameters of the function F on the basis of the updated data sets in the data set storage unit 144. Then, the sight movement amount calculation unit 1543 uses the function F to calculate the amount of sight movement $F(\Delta_{(n\ to\ now)})$ on the screen that corresponds to the eyeball motion amount of the user. Next, the sight position estimation unit 155 adds the amount of sight movement $F(\Delta_{(n\ to\ now)})$ to the position P(n) of the interaction target immediately before the sight position P(now) of the user to estimate the sight position P(now) of the user.

Here, update of the parameters of the function F will be described. In the estimation apparatus 10, an upper limit is provided for the number of data sets stored on the data set storage unit 144, and the one oldest data set among the data sets is discarded in a case in which the number of data sets exceeds the upper limit. In other words, the estimation apparatus uses only the recent interactions and always updates the association between the total amount of change in eye potential Δ and the position P of the interaction target on the screen. It is possible to adapt a change in association due to drifts and posture movement occurring with elapse of time in accordance with this, by carrying out learning using the updated data sets and updating the parameters of the function F.

Figure 7:
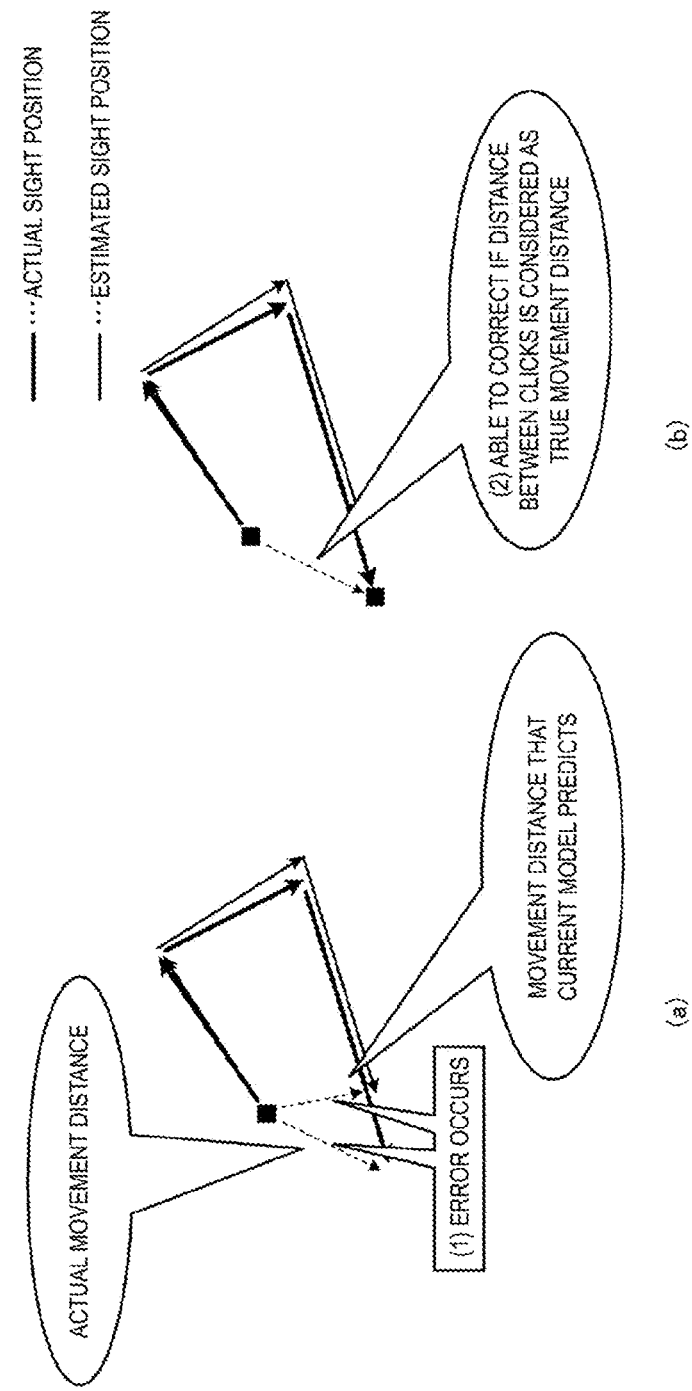
FIGS. 7(a) and 7(b) are diagrams for explaining update of a parameter of a function used by the estimation apparatus illustrated in FIG. 1.

FIGS. 7(a) and 7(b) are diagrams for explaining update of parameters of the function F used by the estimation apparatus 10 illustrated in FIG. 1. Even in a case in which an error has occurred between an actual movement distance of the sight and a movement distance predicted by the current model (function F) on the screen M (see (1) of FIG. 7(a)), it is possible to correct (update) the model (parameters of the function F) by regarding the distance between actual clicks as a true movement distance (see (2) of FIG. 7(b)). In other words, the estimation apparatus 10 always updates the parameters of the function F using the latest position of the interaction target on the screen.

Thus, according to the estimation apparatus 10, the update of the parameters of the function F is automatically repeatedly executed. The user is thus not required to perform any operation to update the parameters of the function F. As described above, the estimation apparatus 10 can reduce degradation of estimation accuracy and also prevent degradation of practical usability due to execution of update of the parameters because the update of the parameters of the function F is always automatically repeated using the latest data sets.

Processing Procedure for Estimation Processing

Figure 8:
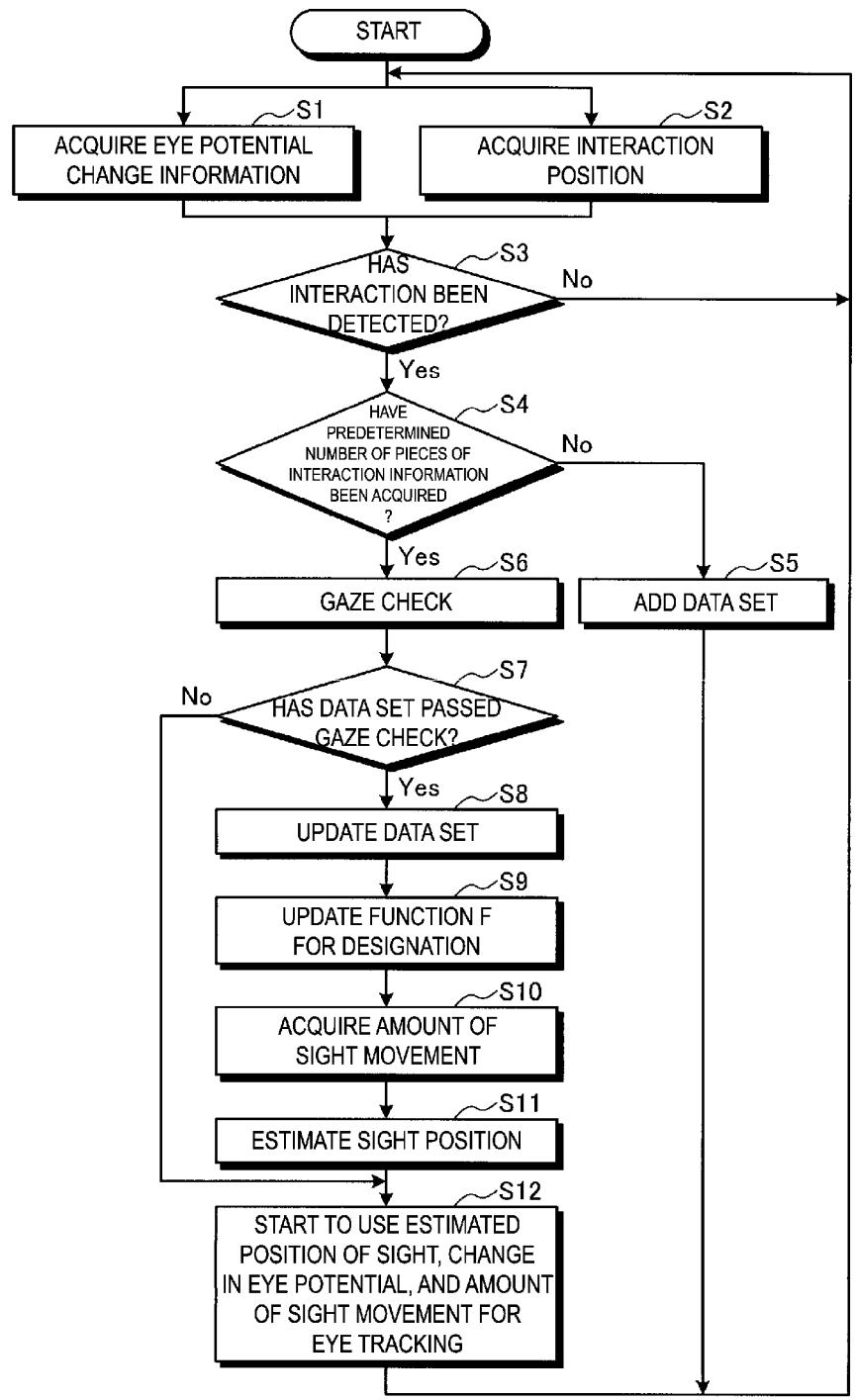
FIG. 8 is a flowchart illustrating a processing procedure for estimation processing according to the first embodiment.

Next, a processing procedure for estimation processing performed by the estimation apparatus 10 will be described. FIG. 8 is a flowchart illustrating a processing procedure for the estimation processing according to the first embodiment.

As illustrated in FIG. 8, the eye potential information acquisition unit 151 acquires the amount of change in eye potential in eyeball motion of the user on the basis of a measurement value of the eye potential of the user input by the sensor 4 (Step S1). For example, the interaction position acquisition unit 152 acquires positional information of an interaction target on the screen that corresponds to an interaction performed on a device through an operation of the user in parallel with Step S1 (Step S2).

In the estimation apparatus 10, the control unit 15 determines whether or not the interaction has been detected (Step S3). If the control unit 15 determines that no interaction has been detected (Step S3: No), the control unit 15 returns to Step S1 and Step S2.

In a case in which the control unit 15 determines that an interaction has been detected (Step S3: Yes), the data set saving unit 1451 determines whether or not a predetermined amount of data sets have been acquired (Step S4). In accordance with a determination that the predetermined amount of data sets have not been acquired (Step S4: No), the data set saving unit 1451 adds, to the data set storage unit 144, the amount of change in eye potential and the positional information of the interaction target on the screen as one data set (Step S5).

Meanwhile, in accordance with a determination that the data set saving unit 1451 has acquired the predetermined amount of data sets (Step S4: Yes), the gaze check unit 153 performs gaze check (Step S6). The gaze check unit 153 determines whether or not the first distance between the previously estimated sight position of the user on the screen and the actual position of the interaction target on the screen in the new interaction is equal to or less than the predetermined threshold value L. Then, in accordance with a determination that the first distance is equal to or less than the predetermined threshold value L, the gaze check unit 153 determines that the data set of the actual positional information of the interaction target on the screen in the new interaction and the amount of change in eye potential that corresponds to the actual positional information has passed the gaze check.

Then, the gaze check unit 153 determines whether or not the data set of the actual positional information of the interaction target on the screen in the new interaction and the amount of change in eye potential that corresponds to the actual positional information has passed the gaze check (Step S7). In a case in which the gaze check unit 153 determines that the target data set has not passed the gaze check (Step S7: No), the control unit 15 moves on to Step S12 without performing the following processing using the data set.

Meanwhile, in a case in which the gaze check unit 153 determines that the target data set has passed the gaze check (Step S7: Yes), the data set saving unit 1541 adds the data set to the data set storage unit 144 (Step S8) and discards an old data set.

Then, the function generation unit 1542 updates a plurality of data sets that are saved in the data set storage unit 144 and include the new data set and the parameters of the function F for estimating the amount of sight movement (Step S9). Next, the sight movement amount calculation unit 1543 inputs the amount of change in eye potential during a period from the clock time at which the previous interaction occurred to the clock time at which the interaction occurs at a current clock time to the function F and acquires the amount of sight movement on the screen that corresponds to the amount of change in eye potential, namely, the amount of movement from the position of the interaction target in the previous interaction to the position of the sight at the current clock time (Step S10).

The sight position estimation unit 155 estimates the sight position at the current clock time by adding the amount of sight movement on the screen that corresponds to the amount of change in eye potential acquired by the sight movement amount calculation unit 1543 to the target position on the screen in the previous interaction (Step S11).

Thereafter, the control unit 15 starts to use the estimated position of the sight, the amount of change in eye potential, and the amount of sight movement for eye tracking (Step S12) and then returns to Step S1 to move on to the next sight position estimation processing.

Effects of First Embodiment

In this manner, the estimation apparatus 10 according to the first embodiment acquires the amount of change with eye potential information of the user and relatively acquires the amount of sight movement of the user on the screen. Then, the estimation apparatus 10 acquires the positional information (absolute value) of the interaction target on the screen that corresponds to the interaction performed on the device through the operation of the user. Next, the estimation apparatus 10 estimates the sight position of the user on the screen at the current clock time on the basis of the amount of sight movement on the screen (relative value) and the positional information of the interaction target on the screen (absolute value). Specifically, the estimation apparatus 10 adds the amount of sight movement on the screen (relative value) to the positional information of the interaction target on the screen (absolute value) and estimates the sight position of the user on the screen at the current clock time.

Thus, a simple estimation scheme of adding utilization of the interaction to the EOG method and adding the amount of sight movement on the screen (relative value) to the positional information of the interaction target on the screen (absolute value) is employed in the first embodiment. In addition, because the estimation scheme of adding the estimated value to the absolute value is employed, it is also possible to maintain high accuracy in the first embodiment as compared with a case in which only the estimated value is added. It is thus possible to estimate the sight position of the user on the screen at the current clock time without increasing the amount of calculation and thereby to perform sight position measurement with high accuracy without degrading practical usability according to the first embodiment.

Also, the gaze check unit 153 determines whether or not the first distance between the previously estimated sight position of the user on the screen and the position of the interaction target on the screen in the new interaction is equal to or less than the predetermined threshold value in the first embodiment. In other words, the estimation apparatus 10 detects a deviation between the actual sight position and the estimated sight position in the first embodiment. Further, the gaze check unit 153 performs gaze check every time an interaction occurs after the function F is generated in the first embodiment.

Also, the parameters of the function F are repeatedly updated using only data sets with no deviations between actual sight positions and estimated sight positions in the first embodiment. In other words, because data sets that do not match the actual sight positions are not employed, it is possible to appropriately execute the update of the parameters of the function F in the first embodiment.

Also, the latest data set is always used to automatically repeat the update of the parameters of the function F in the first embodiment. In other words, the processing related to the update of the parameters of the function F is performed without any explicit operations of the user. In other words, calibration of the sight position required in a case in which the AC EOG method is applied is repeatedly performed in a form in which the user does not aware of the execution in the first embodiment. Further, it is possible to reduce degradation of estimation accuracy and also to prevent degradation of practical usability due to execution of the update of the parameters of the function F according to the first embodiment. As described above, the estimation apparatus 10 can reduce degradation of estimation accuracy and also prevent degradation of practical usability due to execution of update of the parameters because the update of the parameters of the function F is always automatically repeated using the latest data sets.

As described above, according to the first embodiment, it is possible to perform sight position measurement with high accuracy by applying the AC EOG method without degrading practical usability.

FIRST MODIFICATION EXAMPLE OF FIRST EMBODIMENT

As a modification example of the first embodiment, the gaze check unit 153 may adjust and then use an execution timing of the processing for detecting gaze corresponding to an interaction at the time of the detection in the gaze check processing (Step S6). The gaze check unit 153 executes the gaze check processing at a timing based on characteristic information regarding a stop of eyeball motion of the user.

For example, the gaze check unit 153 can detect that gaze has occurred by determining that the user is gazing at a specific position on the screen on the basis of the fact that the eyeball motion is temporarily stopped. When the gaze check unit 153 checks whether or not the user is gazing at a certain interaction, the gaze check unit 153 does not use the sight position estimated at the clock time at which the interaction occurs as it is and uses gaze detected at a timing close to the clock time at which the interaction occurs. In this manner, an improvement in accuracy of the gaze check is expected. Because the user is typically considered to click the mouse after gazing at the click target, adjusting of the timing is expected to be useful to precisely extract the gaze at the interaction target that is present slightly before the interaction.

Also, meta information of the interaction target may be used in the gaze check processing. In a case in which a target with some meaning such as a button or a text box is present, for example, the gaze check unit 153 causes the target to pass the gaze check. Meanwhile, the gaze check unit 153 regards an input in a case in which a target with meaning is not present as an unintended input and regards the user as not being gazing at any target.

SECOND MODIFICATION EXAMPLE OF FIRST EMBODIMENT

Also, the gaze check unit 153 may adaptively change the threshold value L in accordance with reliability of the function F without using a defined value as the threshold value L in a stationary manner in the gaze check processing. For example, a model right after the estimation is started is generated without strictly asking whether or not the gaze target conforms to the interaction target. Thus, because accuracy of the function F is considered not to be that good right after the estimation is started, the gaze check unit 153 may set the threshold value L to be relatively large and reduce the threshold value L until the threshold value L reaches a specific value as the number of times increases.

It is possible to expect that inappropriate gaze check can be prevented from acting, by changing the threshold value L in accordance with the reliability of the function F in this manner. Also, eye potential data may be filtered in order to reduce drifts occurring in a short time unit which cannot completely be handled and absorbed by recorrection of the function F through the update of the data sets.

Second Embodiment

Next, a second embodiment will be described. The second embodiment is adapted to address a change in posture occurring in a short time unit, which cannot completely be absorbed by updating of the parameters of the function F through updating of data sets, using results of detection of a sensor configured to measure the amount of head motion in addition to the eye potential sensor.

Figure 9:
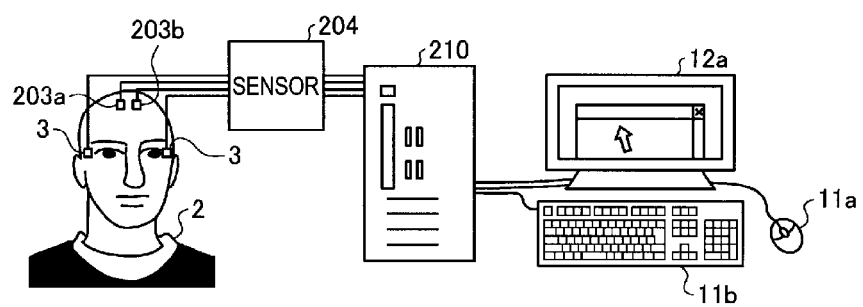
FIG. 9 is a diagram illustrating an example of a configuration of an estimation system according to a second embodiment.

FIG. 9 is a diagram illustrating an example of a configuration of an estimation system according to the second embodiment. As illustrated in FIG. 9, an acceleration sensor 203*a* and an inclination sensor 203*b* are attached to the head of the user 2. The sensor 204 inputs measurement values acquired from the acceleration sensor 203*a* and the inclination sensor 203*b* to the estimation apparatus 210.

The acceleration sensor 203*a* measures acceleration of the head. The acceleration measured by the acceleration sensor 203*a* is information regarding relative three-dimensional position movement of the head. The inclination sensor 203*b* measures a change in angles of the head. The change in angle of the head measured by the inclination sensor 203*b* is information regarding a relative change in angles related to three axes of the head. These two pieces of information are handled as head motion information regarding the amount of relative motion of the head in a space. The estimation apparatus 210 obtains the sight position on the screen using the head motion information along with the amount of change in eye potential.

Figure 10:
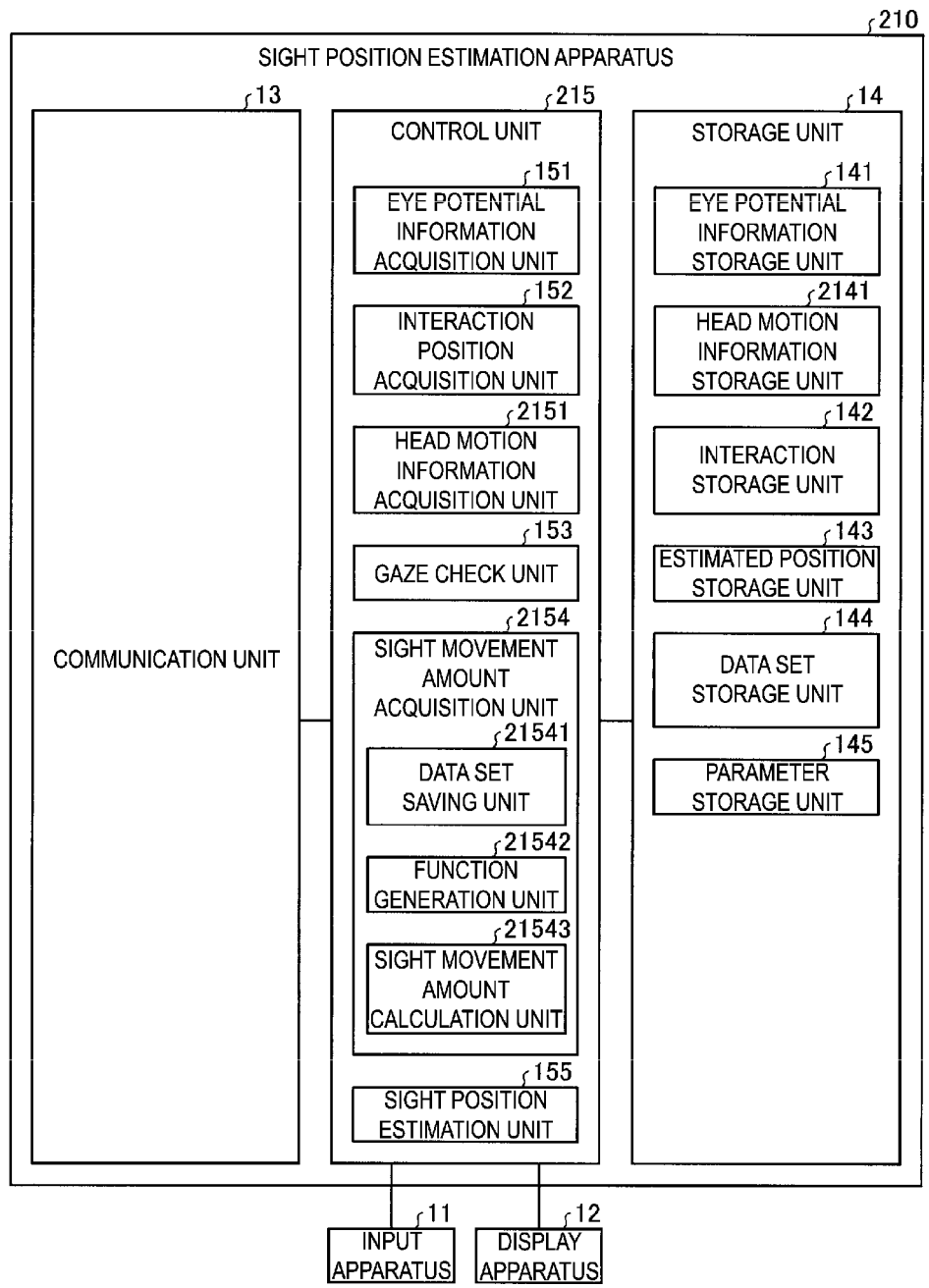
FIG. 10 is a block diagram illustrating an example of a configuration of an estimation apparatus illustrated in FIG. 9.

FIG. 10 is a block diagram illustrating an example of a configuration of the estimation apparatus 210 illustrated in FIG. 9. The estimation apparatus 210 is adapted such that the storage unit 14 has a head motion information storage unit 2141 configured to store head motion information input from the sensor 204 as compared with the estimation apparatus 10 illustrated in FIG. 2. Also, the estimation apparatus 210 has a control unit 215 that has a head motion information acquisition unit 2151 and a sight movement amount acquisition unit 2154 instead of the control unit 15 of the estimation apparatus 10.

The head motion information acquisition unit 2151 acquires head movement information of the user on the basis of measurement values regarding movement of the head of the user. The head motion information acquisition unit 2151 acquires, as head motion information, measurement values obtained by the acceleration sensor 203*a* and the inclination sensor 203*b*.

The sight movement amount acquisition unit 2154 acquires the amount of sight movement on the screen using the head motion information of the user along with the information of the eyeball motion of the user and the positional information of the interaction target on the screen and estimates the sight position of the user on the screen. The sight movement amount acquisition unit 2154 has a data set saving unit 21541, a function generation unit 21542, and a sight movement amount calculation unit 21543.

The data set saving unit 21541 saves, in the data set storage unit 144 at this timing, the information of the eyeball motion of the user acquired by the eye potential information acquisition unit 151, the positional information of the interaction target on the screen acquired by the interaction position acquisition unit 152, and the head motion information of the user acquired by the head motion information acquisition unit 2151 as one data set. The data set saving unit 21541 saves the amount of change in eye potential of the user that has passed through the gaze check unit 153, the positional information of the interaction target on the screen, and the head motion information of the user in the data set storage unit 144 and discards one old data set.

The function generation unit 21542 generates a function F' when the number of data sets saved in the data set storage unit 144 exceeds a predetermined number. The function F' is a function that outputs, as the amount of sight movement, the amount of movement (a distance and a direction) (relative value) from the position of the interaction target in a previous interaction to the position of the sight at a current clock time if the amount of change in eye potential and the head motion information from the clock time at which the previous interaction occurred to the current clock time are input.

The function generation unit 21542 generates the function F' by causing an arbitrary algorithm to learn the plurality of data sets saved in the data set storage unit 144. The function generation unit 21542 stores parameters of the generated function F' in the parameter storage unit 145. Also, the function generation unit 1542 updates the parameters of the function F' every time the data sets are updated with a new data set after the function F' is generated.

The sight movement amount calculation unit 21543 calculates the amount of sight movement on the screen that corresponds to the eyeball motion amount of the user and the head motion information of the user on the basis of the information of the eyeball motion and the head motion information of the user. Specifically, the sight movement amount calculation unit 21543 calculates the amount of movement from the position of the interaction target in the previous interaction to the position of the sight at the current clock time by inputting, to the function F', the amount of change in eye potential and the head motion information from the clock time at which the previous interaction occurred to the current clock time.

Then, the sight position estimation unit 155 obtains the estimated position of the sight position at the current clock time by adding the amount of sight movement on the screen that corresponds to the amount of change in eye potential and the head motion information of the user acquired by the sight movement amount calculation unit 21543 to the target position of the previous interaction on the screen.

Processing Procedure for Estimation Processing

Figure 11:
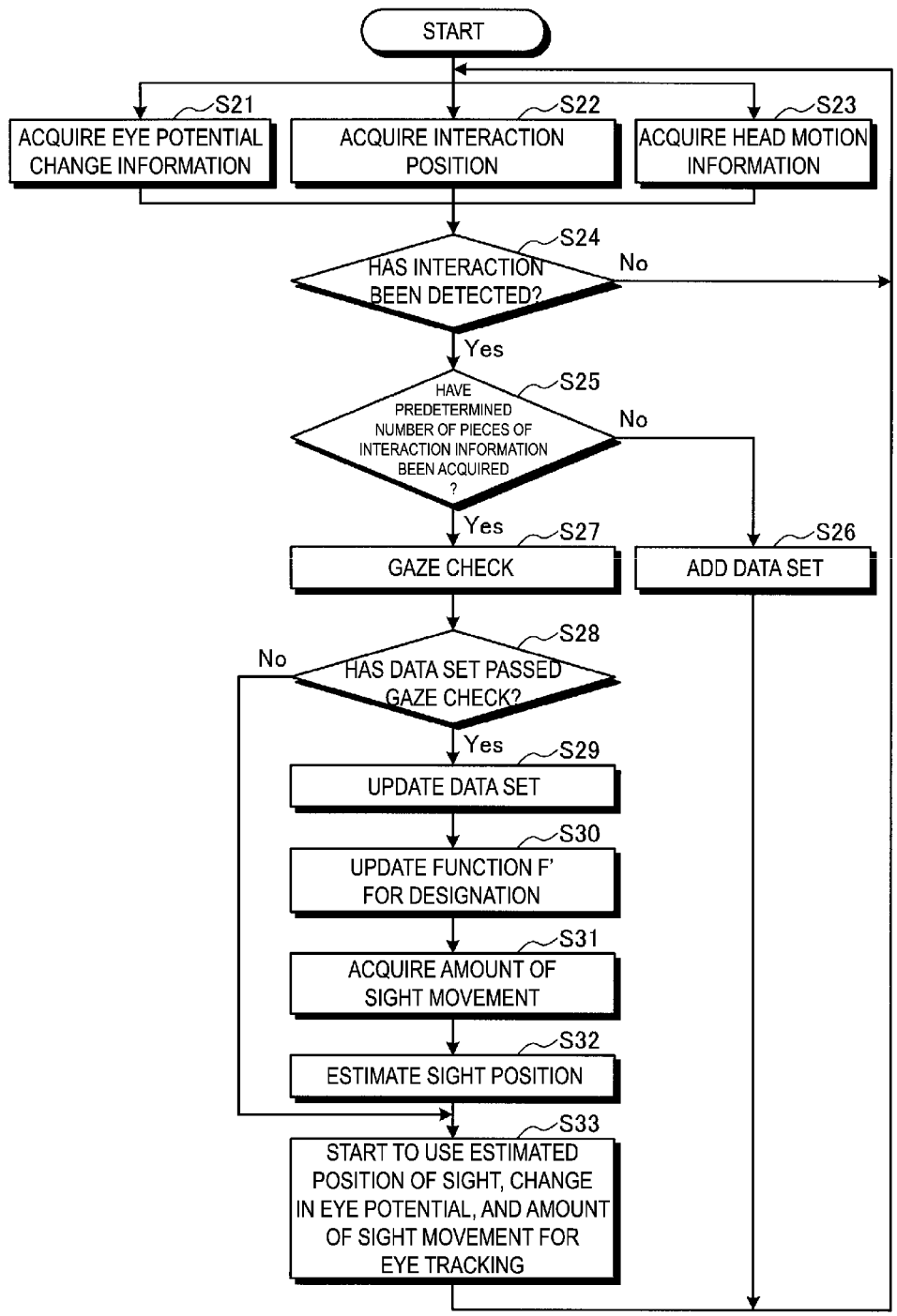
FIG. 11 is a flowchart illustrating a processing procedure for estimation processing according to the second embodiment.
Figure 12:
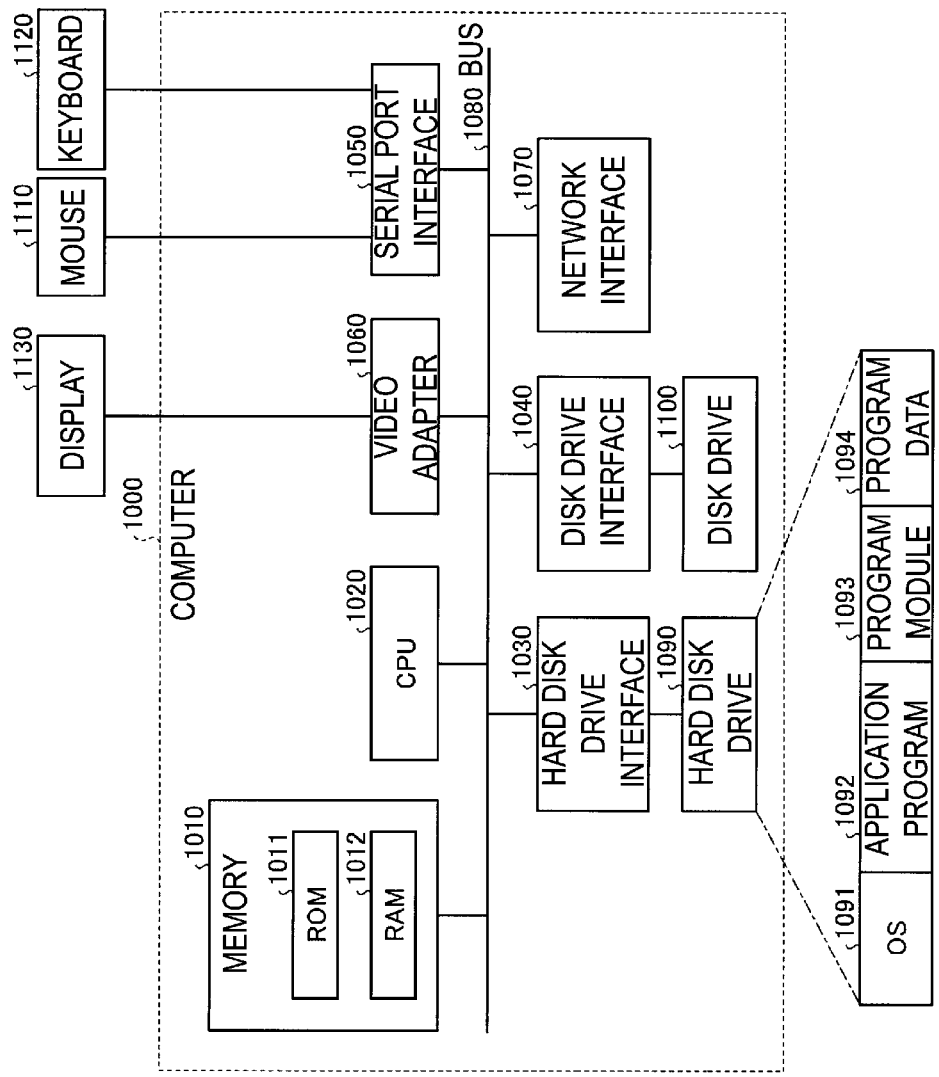
FIG. 12 is a diagram illustrating an example of a computer that realizes an estimation apparatus by executing a program.
Figure 13:
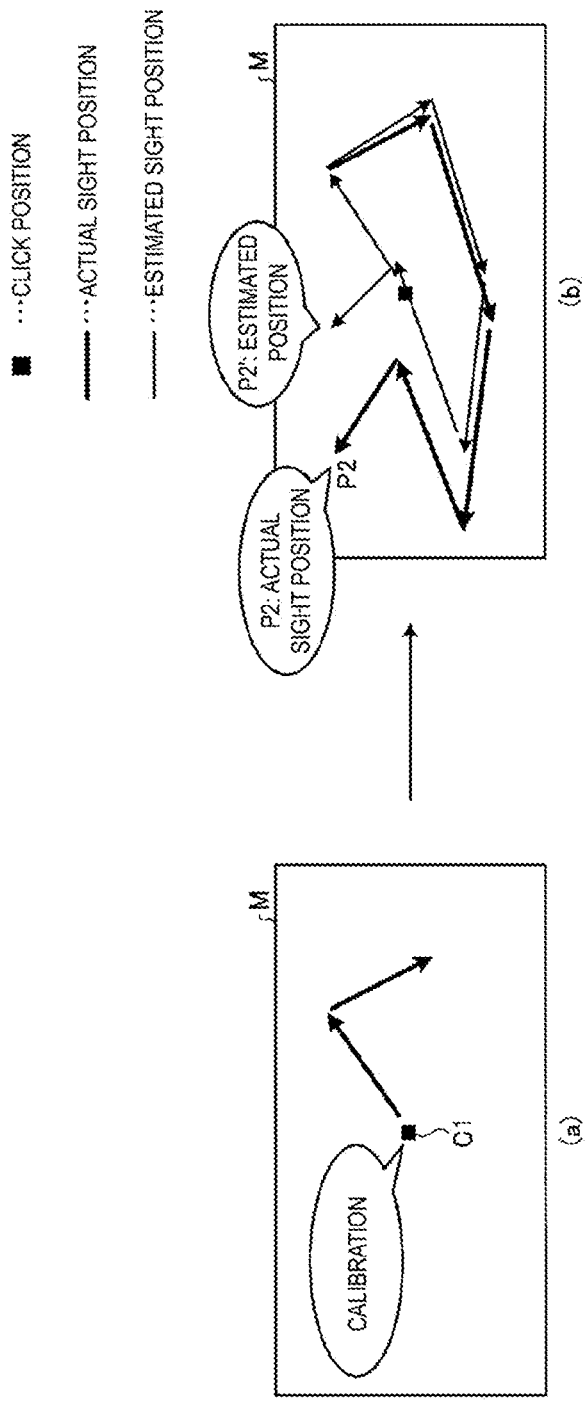
FIGS. 13(a) and 13(b) are diagrams for explaining a sight position estimation method in the related art.

Next, a processing procedure for estimation processing performed by the estimation apparatus 210 will be described. FIG. 11 is a flowchart illustrating a processing procedure for estimation processing according to the second embodiment.

Steps S21 and S22 illustrated in FIG. 11 are processing that is similar to Steps S1 and S2 illustrated in FIG. 8. In parallel with Steps S21 and S22, the head motion information acquisition unit 2151 acquires head motion information of the user (Step S23). Steps S24 and S25 are processing that is similar to Steps S3 and S4 illustrated in FIG. 8.

In accordance with a determination that a predetermined amount of data sets have not been acquired (Step S25: No), the data set saving unit 21451 adds, to the data set storage unit 144, the amount of change in eye potential, the positional information of the interaction target on the screen, and the head motion information as one data set (Step S26).

Meanwhile, in accordance with a determination that the data set saving unit 1451 has acquired the predetermined amount of data sets (Step S25: Yes), the processing proceeds to Step S27. Steps S27 and S28 are processing that is similar to Steps S6 and S7 illustrated in FIG. 8.

In a case in which the gaze check unit 153 determines that the target data set does not pass the gaze check (Step S28: No), the control unit 215 moves on to Step S33 without performing the following processing using the data set.

Meanwhile, in a case in which the gaze check unit 153 determines that the target data set has passed the gaze check (Step S28: Yes), the data set saving unit 21541 adds the data set to the data set storage unit 144 (Step S29) and discards an old data set.

Then, the function generation unit 21542 updates the plurality of data sets that are stored in the data set storage unit 144 and include the new data set parameters of the function F' for estimating the amount of sight movement (Step S30). Next, the sight movement amount calculation unit 1543 inputs the amount of change in eye potential and head movement information from the clock time at which the previous interaction occurred to the clock time at which the interaction at the current clock time occurs to the function F' and acquires the amount of sight movement on the screen that corresponds to the amount of change in eye potential and the head movement information (Step S31). Steps S32 and S33 are processing that is similar to Steps S11 and S12 illustrated in FIG. 8.

Effects of Second Embodiments

Thus, according to the second embodiment, it is possible to acquire the head motion information and to perform sight estimation in consideration of the amount of motion of the head itself where the eyeballs are present in addition to the amount of motion of the eyeballs. The second embodiment has thus an effect that it is possible to further address sight movement with head movement as compared with the first embodiment.

Also, according to the second embodiment, it is possible to obtain information that the sight is directed to a peripheral environment outside the display on the basis of the amount of movement and inclination of the head. According to the second embodiment, it is also possible to measure gaze at an object disposed on a desk by associating the object with an action of gazing at the outside of the display. For example, it is possible to determine that the user is gazing at "a keyboard" if the sight is directed to "the side right below and away from the display", to determine that the user is gazing at "an operation manual near the keyboard" if the sight is directed to "the slightly right side of the side right below the display", and to determine that the user is gazing at "a phone" if the sight is directed to "the left side of the display", As described above, the second embodiment makes it possible to overcome the problem of the related art eye tracker that sight cannot be estimated if a face surface deviates from the screen front direction and to acquire a wider range of data in regard to states of the user.

Note that when the head position is located so as to be vertical to the center of the screen, the vicinity of the center of the screen is located close to the head while the periphery is located far from the head. Such differences in distance lead to differences in association between the eyeball motion amount and the amount of sight movement.

Thus, according to the first and second embodiments, an absolute position of a previous click that is regarded as a start point of eyeball motion on the screen is employed as a part of inputs for generating a function when the sight position is estimated. Thus, in a case in which the head position is located so as to be vertical to the center of the screen for the last several minutes, for example, it is possible to create such a function that the amount of sight movement is calculated to be a small value when the sight moves from a click (start point) in the vicinity of the center of the screen while the amount of sight movement is calculated to be a large value when the sight moves from a click away from the center. Also, in a case in which the head position in the last several minutes is located slightly on the right side of the center of the screen, such a function that the amount of sight movement increases as the sight moves away from the location (slightly on the right side of the center of the screen) at the center is obtained. In other words, it is only necessary to take absolute coordinates of a click into consideration when the eyeball motion amount is associated with the amount of sight movement, and it is also possible to state that the head sensor is not necessarily needed in order to obtain a function in consideration of the head position.

System Configuration and the Like

The components of each apparatus illustrated in the drawing are functional and conceptual components and are not necessarily physically configured as illustrated in the drawing. That is, specific configurations of dispersion and integration of the apparatuses are not limited to those illustrated in the drawing, and all or some of them can be configured to be functionally or physically dispersed and integrated in any unit in accordance with various loads, usage conditions, and the like. Further, all or some of processing functions performed by the apparatuses may be realized by a CPU and a program analyzed and executed by the CPU, or may be realized as hardware by wired logic. The estimation apparatuses 10 and 210 according to the embodiments can also be realized by a computer and a program, and it is also possible to record the program in a recording medium and to provide the program through a network.

Also, all or some parts of the processing described as being automatically performed, in the processing described in the embodiments, can also be manually performed, or all or some parts of the processing described as being manually performed can also be automatically performed by known methods. In addition, information including the processing procedures, the control procedures, the specific names, and various data and parameters described in the above-described document and drawings can be arbitrarily changed except for the case of special description.

Program

FIG. 11 is a diagram illustrating an example of a computer that realizes the estimation apparatuses 10 and 210 by executing a program. A computer 1000 includes, for example, a memory 1010 and a CPU 1020. In addition, the computer 1000 includes a hard disk drive interface 1030, a disk drive interface 1040, a serial port interface 1050, a video adapter 1060, and a network interface 1070. These units are connected by a bus 1080.

The memory 1010 includes a read only memory (ROM) 1011 and a RAM 1012. The ROM 1011 stores a boot program, such as Basic Input Output System (BIOS), for example. The hard disk drive interface 1030 is connected to a hard disk drive 1090. The disk drive interface 1040 is connected to a disk drive 1100. A detachable storage medium such as a magnetic disk or an optical disc is inserted into the disk drive 1100. The serial port interface 1050 is connected to, for example, a mouse 1110 and a keyboard 1120. A video adapter 1060 is connected to, for example, a display 1130.

Here, the hard disk drive 1090 stores, for example, an OS 1091, an application program 1092, a program module 1093, and program data 1094. In other words, the program that defines the processing of the estimation apparatuses 10 and 210 is implemented as a program module 1093 in which codes that are executable by the computer 1000 are described. The program module 1093 is stored in, for example, the hard disk drive 1090. For example, the program module 1093 for executing processing similar to the functional configurations of the estimation apparatuses 10 and 210 is stored in the hard disk drive 1090. Note that the hard disk drive 1090 may be replaced by a solid state drive (SSD).

In addition, setting data used in the processing of the above-described embodiment is stored in, for example, the memory 1010 or the hard disk drive 1090, as the program data 1094. In addition, the CPU 1020 reads the program module 1093 and the program data 1094 stored in the memory 1010 and the hard disk drive 1090 to the RAM 1012 and executes them as necessary.

Note that the program module 1093 and the program data 1094 are not limited to being stored in the hard disk drive 1090, and may be stored, for example, in a removable storage medium, and read by the CPU 1020 via a disk drive 1100 or its equivalent. Alternatively, the program module 1093 and the program data 1094 may be stored in another computer connected to the computer 100 through a network (a LAN, a wide area network (WAN), or the like). In addition, the program module 1093 and the program data 1094 may be read by the CPU 1020 from another computer through the network interface 1070.

Although the embodiments to which the present invention achieved by the present inventor is applied have been described above, the present invention is not limited by the description and the drawings that are parts of the disclosure of the present invention based on the embodiments. In other words, all of other embodiments, examples, running techniques, and the like achieved by those skilled in the art on the basis of the embodiments are included in the scope of the present invention.

REFERENCE SIGNS LIST

3 Electrode
4 Sensor
10, 210 Estimation apparatus
11 Input apparatus
11a Mouse
11b Keyboard
12 Display apparatus
12a Display
13 Communication unit
14 Storage unit
15, 215 Control unit
141 Eye potential information storage unit
142 Interaction storage unit
143 Estimated position storage unit
144 Data set storage unit
145 Parameter storage unit
151 Eye potential information acquisition unit
152 Interaction position acquisition unit
153 Gaze check unit
154,2154 Sight movement amount acquisition unit
155 Sight position estimation unit
1541, 21541 Data set saving unit
1542, 21542 Function generating unit
1543, 21543 Sight movement amount calculation unit
2141 Head motion information storage unit

The invention claimed is:

1. An estimation method comprising:
acquiring information of an eyeball motion of a user based on a measurement value of an eye potential of the user;
acquiring positional information of an interaction target on a screen that corresponds to an interaction performed on a device through an operation of the user;
acquiring information regarding a relative motion of sight of the user based on at least of the information of the eyeball motion of the user; and
estimating a sight position of the user on the screen based on the information regarding the relative motion of the sight of the user and the positional information of the interaction target on the screen, by processing circuitry, comprising:
   determining whether or not a first distance between a previously estimated sight position of the user on the screen and a position of an interaction target on the screen corresponding to a new interaction is equal to or less than a predetermined threshold value; and
   in accordance with determining that the first distance is equal to or less than the predetermined threshold value, estimating the sight position of the user on the screen based on positional information of the interaction target on the screen that corresponds to the new interaction and information regarding the relative motion of the sight of the user that corresponds to the positional information; and
   in accordance with determining that the first distance is greater than the predetermined threshold value, estimating the sight position of the user on the screen based on positional information of the interaction target on the screen on which the first distance is determined to be equal to or less than the predetermined threshold value in determining immediately before the new interaction and information regarding the relative motion of the sight of the user that corresponds to the positional information.

2. The estimation method according to claim 1, wherein the determining is executed at a timing based on characteristic information regarding a stop of the eyeball motion of the user.

3. The estimation method according to claim 1,
wherein the acquiring information regarding the relative motion of sight of the user includes:
saving, in a data set, the information of the eyeball motion of the user and the positional information of the interaction target on the screen, and
acquiring an amount of sight movement on the screen that corresponds to an eyeball motion amount of the user based on the information of the eyeball motion of the user and the positional information of the interaction target on the screen that are present in the data set.

4. The estimation method according to claim 3, wherein the saving includes storing positional information of the interaction target on the screen in the new interaction, the first distance of which has been determined to be equal to or less than the predetermined threshold value in the determining, and information of an eyeball motion that corresponds to the new interaction in the data set at this timing.

5. The estimation method according to claim 3, further including:
acquiring head movement information of the user based on a measurement value regarding movement of a head of the user,
wherein the acquiring heading movement information includes acquiring the amount of sight movement on the screen using the head movement information of the user along with the information of the eyeball motion of the user and the positional information of the interaction target on the screen.

6. A non-transitory computer-readable recording medium storing therein an estimation program that causes a computer to execute a process comprising:
acquiring information of an eyeball motion of a user based on a measurement value of an eye potential of the user;
acquiring positional information of an interaction target on a screen that corresponds to an interaction performed on a device through an operation of the user;
acquiring information regarding a relative motion of sight of the user based on at least of the information of the eyeball motion of the user; and
estimating a sight position of the user on the screen based on the information regarding the relative motion of the sight of the user and the positional information of the interaction target on the screen, comprising:
   determining whether or not a first distance between a previously estimated sight position of the user on the screen and a position of an interaction target on the screen corresponding to a new interaction is equal to or less than a predetermined threshold value; and
   in accordance with determining that the first distance is equal to or less than the predetermined threshold value, estimating the sight position of the user on the screen based on positional information of the interaction target on the screen that corresponds to the new interaction and information regarding the relative motion of the sight of the user that corresponds to the positional information; and
   in accordance with determining that the first distance is greater than the predetermined threshold value, estimating the sight position of the user on the screen based on positional information of the interaction target on the screen on which the first distance is determined to be equal to or less than the predetermined threshold value in determining immediately before the new interaction and information regarding the relative motion of the sight of the user that corresponds to the positional information.

7. An estimation apparatus comprising:

a memory; and processing circuitry coupled to the memory and configured to:

acquire information of an eyeball motion of a user based on a measurement value of an eye potential of the user;

acquire positional information of an interaction target on a screen that corresponds to an interaction performed on a device through an operation of the user;

acquire information regarding a relative motion of sight of the user based on at least of the information of the eyeball motion of the user; and estimate a sight position of the user on the screen based on the information regarding the relative motion of the sight of the user and the positional information of the interaction target on the screen, comprising:

determining whether or not a first distance between a previously estimated sight position of the user on the screen and a position of an interaction target on the screen corresponding to a new interaction is equal to or less than a predetermined threshold value; and in accordance with determining that the first distance is equal to or less than the predetermined threshold value, estimating the sight position of the user on the screen based on positional information of the interaction target on the screen that corresponds to the new interaction and information regarding the relative motion of the sight of the user that corresponds to the positional information; and in accordance with determining that the first distance is greater than the predetermined threshold value, estimating the sight position of the user on the screen based on positional information of the interaction target on the screen on which the first distance is determined to be equal to or less than the predetermined threshold value in determining immediately before the new interaction and information regarding the relative motion of the sight of the user that corresponds to the positional information.

* * * * *